(12) United States Patent
Nordh

(10) Patent No.: US 8,945,094 B2
(45) Date of Patent: Feb. 3, 2015

(54) APPARATUS AND METHOD FOR MEDICATION DELIVERY USING SINGLE INPUT-SINGLE OUTPUT (SISO) MODEL PREDICTIVE CONTROL

(75) Inventor: Pernell E. T. Nordh, Calgary (CA)

(73) Assignee: Honeywell International Inc., Morristown, NJ (US)

( * ) Notice: Subject to any disclaimer, the term of this patent is extended or adjusted under 35 U.S.C. 154(b) by 532 days.

(21) Appl. No.: 12/877,795

(22) Filed: Sep. 8, 2010

(65) Prior Publication Data

US 2012/0059351 A1    Mar. 8, 2012

(51) Int. Cl.
| | |
|---|---|
| *A61K 9/22* | (2006.01) |
| *A61M 5/172* | (2006.01) |
| *A61M 5/142* | (2006.01) |

(52) U.S. Cl.
CPC ......... *A61M 5/1723* (2013.01); *A61M 5/14244* (2013.01); *A61M 2205/3561* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2230/06* (2013.01); *A61M 2230/201* (2013.01); *A61M 2230/30* (2013.01)
USPC ............. 604/890.1; 604/66; 604/67; 604/504

(58) Field of Classification Search
USPC ................ 604/65–67, 503, 504, 890.1, 891.1
See application file for complete search history.

(56) References Cited

U.S. PATENT DOCUMENTS

| | | | |
|---|---|---|---|
| 4,714,462 A | 12/1987 | DiDomenico | |
| 5,351,184 A | 9/1994 | Lu et al. | |
| 5,572,420 A | 11/1996 | Lu | |
| 6,542,782 B1 | 4/2003 | Lu | |
| 6,558,351 B1 | 5/2003 | Steil et al. | |
| 7,022,072 B2 | 4/2006 | Fox et al. | |
| 7,168,675 B2 | 1/2007 | Cabuz et al. | |
| 7,235,164 B2 | 6/2007 | Anex et al. | |
| 7,267,665 B2 | 9/2007 | Steil et al. | |
| 7,354,420 B2 | 4/2008 | Steil et al. | |
| 7,402,153 B2 | 7/2008 | Steil et al. | |
| 7,547,281 B2 | 6/2009 | Hayes et al. | |
| 7,766,830 B2 | 8/2010 | Fox et al. | |
| 2002/0090738 A1 | 7/2002 | Cozzette et al. | |
| 2002/0107504 A1 | 8/2002 | Gordon | |

(Continued)

OTHER PUBLICATIONS

Robert S. Dinsmoor, "The Artificial Pancreas, How to "close the loop"", JDRF Countdown, Winter 2007, p. 24-25.

(Continued)

*Primary Examiner* — Emily Schmidt

(57) ABSTRACT

A method includes receiving measurements from a sensor associated with a patient at a portable medication delivery device. The method also includes controlling delivery of medication to the patient at the portable medication delivery device using a single input, single output (SISO) model predictive control technique. The SISO model predictive control technique includes predicting a characteristic of the patient using the measurements and a model associated with the patient. The SISO model predictive control technique also includes determining whether the characteristic of the patient is predicted to fall outside of a desired range. In addition, the SISO model predictive control technique includes, if the characteristic of the patient is predicted to fall outside of the desired range, determining an amount of medication to deliver to the patient and delivering the determined amount of medication to the patient.

20 Claims, 2 Drawing Sheets

(56) References Cited

U.S. PATENT DOCUMENTS

| | | | |
|---|---|---|---|
| 2003/0125612 | A1 | 7/2003 | Fox et al. |
| 2003/0130616 | A1 | 7/2003 | Steil et al. |
| 2004/0193025 | A1 | 9/2004 | Steil et al. |
| 2005/0096511 | A1 | 5/2005 | Fox et al. |
| 2005/0096512 | A1 | 5/2005 | Fox et al. |
| 2005/0113653 | A1 | 5/2005 | Fox et al. |
| 2005/0187515 | A1 | 8/2005 | Varrichio et al. |
| 2006/0016701 | A1 | 1/2006 | Qin et al. |
| 2006/0173406 | A1 | 8/2006 | Hayes et al. |
| 2006/0224109 | A1 | 10/2006 | Steil et al. |
| 2006/0272652 | A1 | 12/2006 | Stocker et al. |
| 2007/0173761 | A1 | 7/2007 | Kanderian, Jr. et al. |
| 2007/0276545 | A1* | 11/2007 | Smirnov ............ 700/282 |
| 2007/0293843 | A1* | 12/2007 | Ireland et al. ......... 604/504 |
| 2008/0097289 | A1 | 4/2008 | Steil et al. |
| 2008/0183060 | A1 | 7/2008 | Steil et al. |
| 2008/0188796 | A1 | 8/2008 | Steil et al. |
| 2008/0275384 | A1* | 11/2008 | Mastrototaro ......... 604/66 |
| 2009/0062767 | A1 | 3/2009 | Van Antwerp et al. |
| 2009/0209911 | A1 | 8/2009 | Cabus et al. |
| 2009/0234213 | A1 | 9/2009 | Hayes et al. |
| 2010/0114015 | A1 | 5/2010 | Kanderian, Jr. et al. |

OTHER PUBLICATIONS

Stuart A. Weinzimer, MD, et al., "Fulty Automated Closed-Loop Insulin Delivery vs. Semi-Automated Hybrid Control in Pediatric Patients with Type 1 Diabetes using an Artificial Pancreas", Diabetes Care Publish Ahead of Print, pubtised online Feb. 5, 2008, 14 pages.

Garry Steil, et al., "Metabolic modeling and the closed-loop insulin delivery problem", Diabetes Research and Clinical Practice 74 (2006), p. S183-S186.

Antonios E. Panteleon, et al., "Evaluation of the Effect of Gain on the Meal Response of an Automated Closed-Loop Insulin Delivery System", Diabetes, vol. 55, Jul. 2006, p. 1995-2000.

Sami S. Kanderian, M.S., et al., "Identification ot Intraday Metabolic Profiles during Closed-Loop Glucose Controt in Individuals with Type 1 Diabetes", Journal of Diabetes Science and Technology, vol. 3, Issue 5, Sep. 2009, p. 1047.

Garry M. Steil, Ph.D., et al, "Intensive Care Unit Insulin Delivery Algorithms: Why So Many? How to Choose?", Journal of Diabetes Science and Technology, vol. 3, Issue 1, Jan. 2000, p. 125-140.

Stuart A. Weinzimer, MD, "Closed Loop Studies in Children", Artificial Pancreas Workshop, Jul. 21-22, 2008, 21 pages.

"Obstacles and Opportunities on the Road to an Artificial Pancreas: Closing the Loop", Summary Report, National Institutes of Health (NIH) and Juvenile Diabetes Research Foundation (JDRF) Workshop in Collaboration with the Food and Drug Administration (FDA), Dec. 19, 2005, p. 1-16.

Wijaya Martanto et al., "Transdermal Delivery of Insulin Using Microneedles in Vivo", Pharmaceutical Research, vol. 21, No. 6, Jun. 2004, pp. 947-952.

Shawn P. Davis et al., "The Mechanics of Microneedles", Proceedings of the Second Joint EMBS/BMES Conference, Houston, TX USA, Oct. 23-26, 2002, IEEE, pp. 498-499.

Shawn P. Davis et al., "Hollow Metal Microneedles for Insulin Delivery to Diabetic Rats", IEEE Transactions on Biomedical Engineering, vol. 52, No. 5, May 2005, pp. 909-915.

Jeffrey D. Zahn et al., "Continuous On-Chip Micropumping for Microneedle Enhanced Drug Delivery", Biomedical Microdevices 6:3, 2004, pp. 183-190.

Reference Manual "H-TRONplus", Disetronic Medical Systems, Inc., 1999, 63 pages.

* cited by examiner

APPARATUS AND METHOD FOR MEDICATION DELIVERY USING SINGLE INPUT-SINGLE OUTPUT (SISO) MODEL PREDICTIVE CONTROL

TECHNICAL FIELD

This disclosure relates generally to medication delivery systems. More specifically, this disclosure relates to an apparatus and method for medication delivery using single input-single output (SISO) model predictive control.

BACKGROUND

Various medication delivery devices are used to supply medication to patients. For example, insulin pumps can be used to deliver insulin for patients with Type 1 diabetes mellitus. Many insulin pumps use open-loop control, meaning a pump typically delivers medication based on a fixed setpoint without any feedback of a patient's actual condition. However, as medical technology advances, new and more accurate sensors continue to improve the patient information that is available for use. Some sensors are even capable of providing real-time data, such as continuous glucose monitoring (CGM) sensors that provide continuous readings of blood glucose levels in diabetic patients.

SUMMARY

This disclosure provides an apparatus and method for medication delivery using single input-single output (SISO) model predictive control.

In a first embodiment, a method includes receiving measurements from a sensor associated with a patient at a portable medication delivery device. The method also includes controlling delivery of medication to the patient at the portable medication delivery device using a single input, single output (SISO) model predictive control technique. The SISO model predictive control technique includes predicting a characteristic of the patient using the measurements and a model associated with the patient. The SISO model predictive control technique also includes determining whether the characteristic of the patient is predicted to fall outside of a desired range. In addition, the SISO model predictive control technique includes, if the characteristic of the patient is predicted to fall outside of the desired range, determining an amount of medication to deliver to the patient and delivering the determined amount of medication to the patient.

In a second embodiment, an apparatus includes at least one interface configured to receive measurements from a sensor associated with a patient. The apparatus also includes a controller configured to control delivery of medication to the patient using a single input, single output (SISO) model predictive control technique. The SISO model predictive control technique includes predicting a characteristic of the patient using the measurements and a model associated with the patient. The SISO model predictive control technique also includes determining whether the characteristic of the patient is predicted to fall outside of a desired range. The SISO model predictive control technique further includes, if the characteristic of the patient is predicted to fall outside of the desired range, determining an amount of medication to deliver to the patient and initiating delivery of the determined amount of medication to the patient.

In a third embodiment, a computer readable medium embodies a computer program. The computer program includes computer readable program code for receiving measurements from a sensor associated with a patient at a portable medication delivery device. The computer program also includes computer readable program code for controlling delivery of medication to the patient at the portable medication delivery device using a single input, single output (SISO) model predictive control technique. The SISO model predictive control technique includes predicting a characteristic of the patient using the measurements and a model associated with the patient. The SISO model predictive control technique also includes determining whether the characteristic of the patient is predicted to fall outside of a desired range. In addition, the SISO model predictive control technique includes, if the characteristic of the patient is predicted to fall outside of the desired range, determining an amount of medication to deliver to the patient and delivering the determined amount of medication to the patient.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
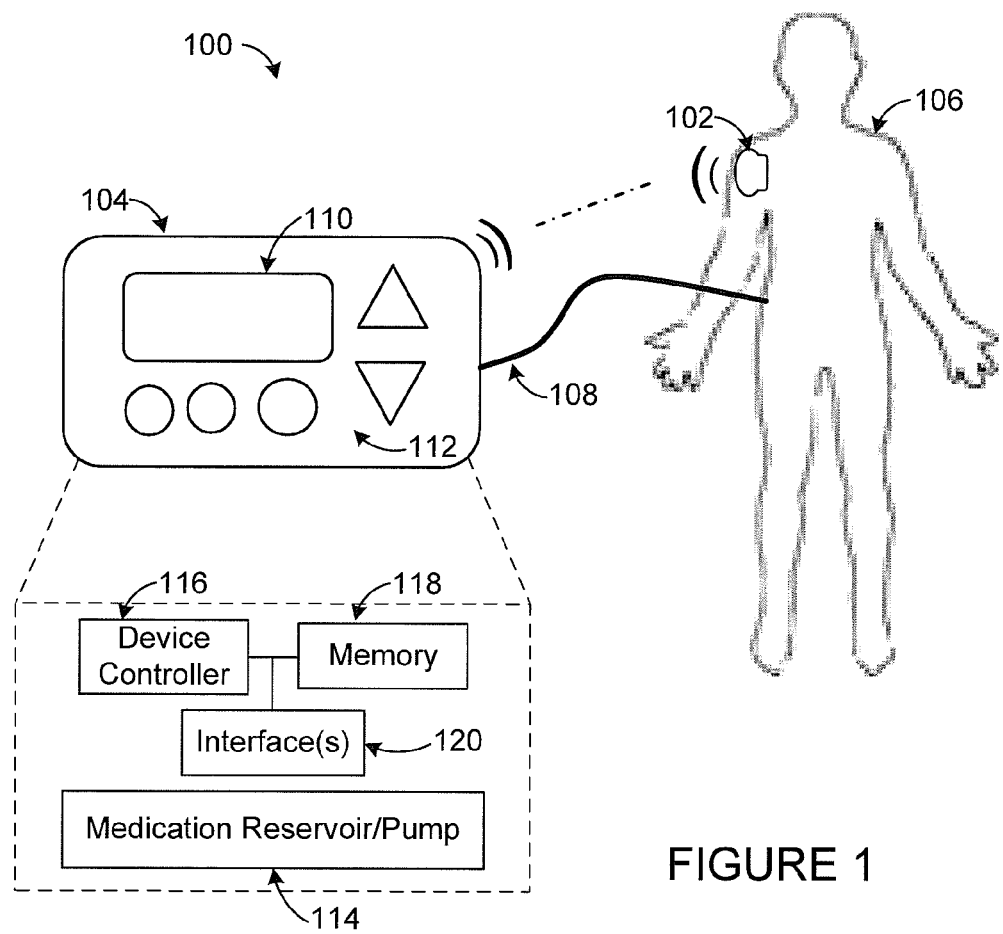
FIG. 1 illustrates an example medication delivery system using single input-single output (SISO) model predictive control according to this disclosure.
Figure 2:
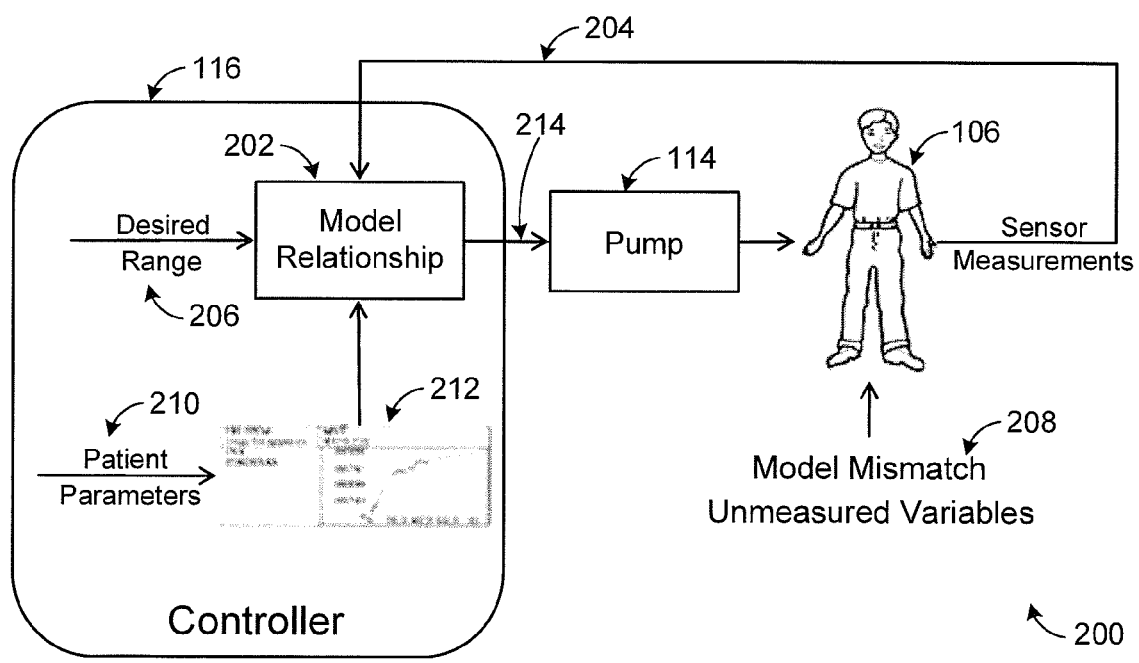
FIG. 2 illustrates an example SISO model predictive control scheme for a medication delivery system according to this disclosure.
Figure 3:
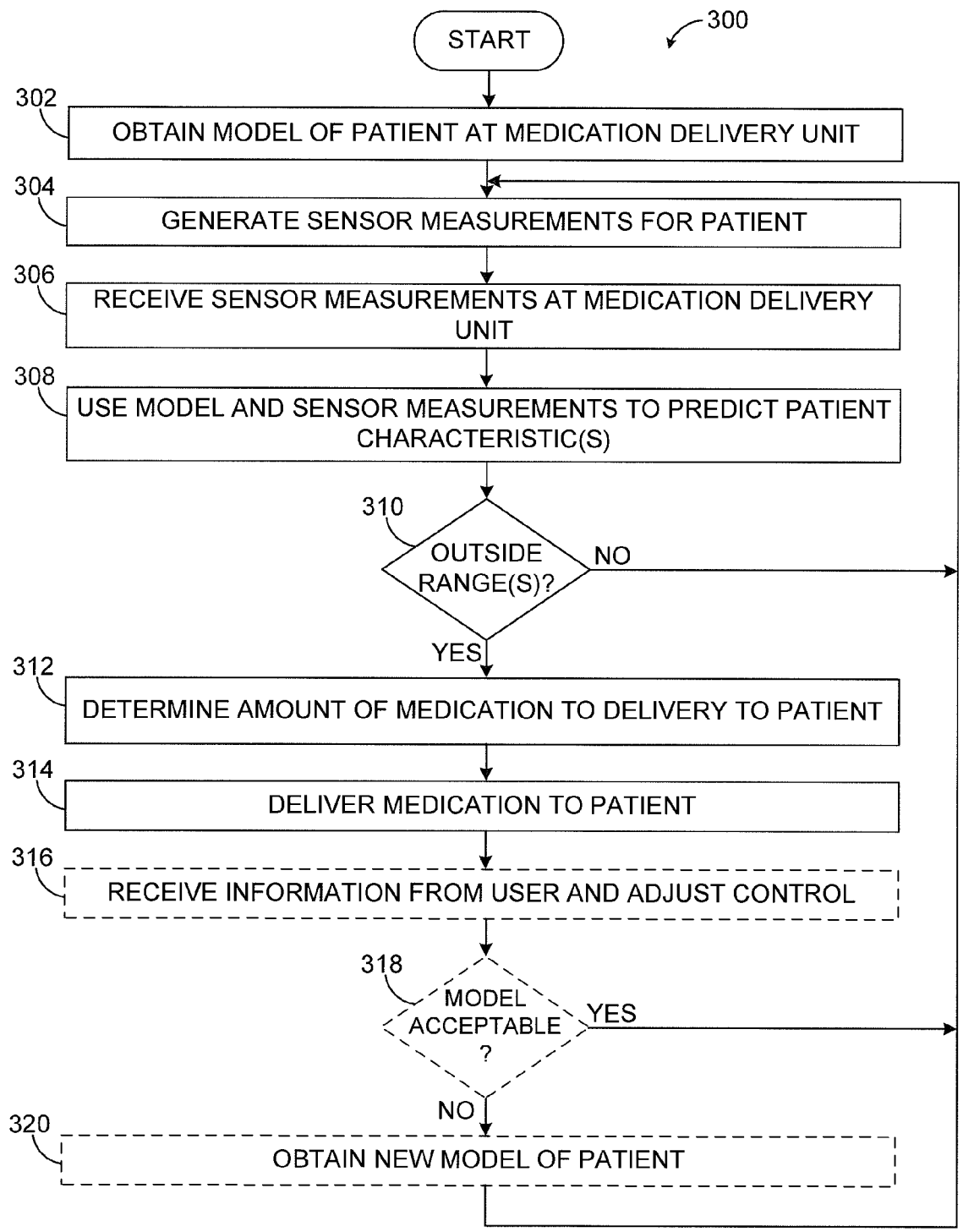
FIG. 3 illustrates an example method for medication delivery using SISO model predictive control according to this disclosure.

FIGS. 1 through 3, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

FIG. 1 illustrates an example medication delivery system 100 using single input-single output (SISO) model predictive control according to this disclosure. In this example embodiment, the system 100 includes a patient monitor 102 and a medication delivery unit 104. The patient monitor 102 is worn by, implanted within, or otherwise associated with a patient 106. The patient monitor 102 can measure one or more characteristics of the patient 106. For example, the patient monitor 102 could measure blood glucose levels in a diabetic patient 106. The patient monitor 102 could detect or measure any other physical characteristic(s) of the patient 106, such as blood pressure, pulse rate, or blood oxygen content. The patient monitor 102 could perform the detection or measuring operations continuously, near-continuously, or intermittently at any suitable interval.

As shown here, the patient monitor 102 communicates with the medication delivery unit 104 using wireless signals. Any suitable wired or wireless signal(s) could be used to transport measurements or other data between the patient monitor 102 and the medication delivery unit 104. For example, the patient monitor 102 may communicate with the medication delivery unit 104 using radio frequency (RF) signals or a wired link.

The patient monitor 102 includes any suitable structure for detecting or measuring any physical characteristic(s) of a patient 106. The patient monitor 102 could, for example, represent a continuous glucose monitoring (CGM) sensor with a wireless transmitter.

The medication delivery unit 104 delivers one or more medications to the patient 106 through a delivery tube 108. For example, the medication delivery unit 104 could be worn by the patient 106, and a portion of the delivery tube 108 could be implanted subcutaneously within the patient 106. The medication delivery unit 104 uses data from the patient monitor 102 to control the supply of medication to the patient 106. In this way, the medication delivery unit 104 supports closed-loop control of medication delivery.

In this example, the medication delivery unit 104 includes a display 110 and one or more controls 112. The display 110 presents various information to the patient 106 or other person, such as a current reading from the patient monitor 102 or any alerts or problems detected. The display 110 includes any suitable structure for presenting information to a user, such as a liquid crystal display (LCD) or a light emitting diode (LED) display. The controls 112 allow a user to invoke certain functions, such as adjustment of medication delivery or programming of the medication delivery unit 104. Each control 112 includes any suitable structure for receiving user input. While shown separately, the display 110 and controls 112 could be integrated, such as when a touch-sensitive display 110 displays one or more soft controls 112.

The medication delivery unit 104 also includes a medication reservoir and pump 114. The reservoir and pump 114 store one or more medications and dispense controlled amounts of the medication(s) into the patient 106. The reservoir and pump 114 include any suitable structure(s) for storing and delivering medication for a patient.

The medication delivery unit 104 further includes a device controller 116, a memory 118, and at least one interface 120. The device controller 116 controls the overall operation of the medication delivery unit 104. For example, the device controller 116 could receive measurements from the patient monitor 102, use model predictive control to estimate how much medication to dispense to the patient 106, and cause the reservoir and pump 114 to dispense the determined amount of medication. The device controller 116 can also implement various constraints, such as by ensuring that no more than a maximum amount of medication is delivered to the patient 106 in a given time period. The device controller 116 includes any suitable structure for controlling operation of a medication delivery device. As particular examples, the device controller 116 could represent a processor, microprocessor, microcontroller, field programmable gate array, digital signal processor, or other processing or control device.

The memory 118 stores information used, generated, or collected by the medication delivery unit 104. For example, the memory 118 could store historical data, such as measurements of the patient's physical characteristic(s) obtained from the patient monitor 102 or dispensed amounts of medication. The memory 118 could also store one or more models used to predict how medication affects the patient 106, which can be used by the device controller 116 to determine how much medication (if any) to administer to the patient 106. The memory 118 could further store instructions executed by the device controller 116. The memory 118 could store any other or additional information. The memory 118 includes any suitable volatile and/or non-volatile storage and retrieval device or devices.

The at least one interface 120 facilitates communication between the medication delivery unit 104 and external devices or systems. For example, an interface 120 could receive data wirelessly from the patient monitor 102. The same or different interface 120 could transmit data to and receive data from an external monitoring or control application, which could track the operation of the medication delivery unit 104 or program the medication delivery unit 104. The at least one interface 120 includes any suitable structure for facilitating communication with one or more external devices or systems, such as a wireless transceiver or a wired network connection.

Closed-loop control of medication delivery is often highly desirable. For example, in patients 106 with Type 1 diabetes mellitus, blood glucose levels could be monitored continuously or semi-continuously by the patient monitor 102, and the measured glucose levels could be used to control insulin delivery by the medication delivery unit 104. However, implementing closed-loop control in a portable medical device for a patient 106 is not a simple task. Among other things, the following two issues affect closed-loop control for medication delivery. First, the dynamics of how medication interacts with and affects the human body, such as how blood sugar and insulin interact within the body, can be highly complex. Process dead-times, variability within a single person's body, and variability across different people's bodies make closed-loop control very difficult. Second, computational efficiency is often difficult. A control algorithm applied to a medical issue often has to execute in a small portable device capable of being worn by a patient. This often prevents, for example, typical industrial process control algorithms from being used in medical applications. This is because typical industrial process control algorithms are often computationally intensive and require powerful processing components for execution. As particular examples, proportional-integral-derivative (PID) control algorithms typically have trouble managing the complex dynamics of medical applications, and multivariable model predictive control algorithms are typically too computationally intensive for medical applications.

In accordance with this disclosure, the medication delivery unit 104 (such as in the device controller 116) implements a single input-single output or "SISO" model predictive control technique. This control technique addresses the complex control dynamics present with medication delivery, as well as handling the computational efficiency of the control problem. The control algorithm executed by the device controller 116 is capable of handling complex dynamics, yet is computationally very efficient. Also, the control algorithm can improve the ease of use and maintenance of the medication delivery unit 104 for both patients and medical staff that have to support the medication delivery unit 104.

The SISO model predictive control algorithm could be implemented in any suitable manner. For example, as described above, the control algorithm could be programmed into the device controller 116. Alternatively, the control algorithm could be implemented using a small adjunct device that is coupled to, mounted on, or otherwise associated with the medication delivery unit 104. Any suitable SISO model predictive control technique could be used in the medication delivery unit 104. Example techniques are disclosed in U.S. Pat. No. 5,351,184; U.S. Pat. No. 5,572,420; and U.S. Pat. No. 6,542,782 (which are all hereby incorporated by reference).

The use of a SISO model predictive control technique can provide various advantages. In addition to handling process complexities without being computationally intensive, the SISO model predictive control technique can help to stabilize medication delivery. That is, the use of SISO model predictive control can help to stabilize the patient's physical characteristic while reducing or minimizing the use of medication. Moreover, it may be simpler to program and set up the medication delivery unit 104. The necessary constraints can be set for the patient 106, the model used by the control algorithm can be selected or defined, and the medication delivery unit 104 can operate using the model and the constraints. This can reduce mistakes and make the startup process easier for patients and medical staff that support and care for them.

Beyond that, no reference trajectory may be required for proper control, further reducing setup and maintenance requirements for the medical staff (who are not usually trained in industrial process control).

In addition, the overall use of the medication delivery unit 104 may be simplified. For example, the control algorithm could allow adjustment of the performance ratio, which represents the "speed" at which the control algorithm responds to changes in its input. Lower performance ratios mean the control algorithm responds more slowly to changes in sensor measurements, while higher performance ratios mean the control algorithm responds more quickly to changes in sensor measurements. This can give the patient 106 a "one-knob" tuning capability for speeding up or slowing down the response time, which greatly simplifies the control tuning since a single number can be adjusted.

Although FIG. 1 illustrates one example of a medication delivery system 100 using SISO model predictive control, various changes may be made to FIG. 1. For example, the system 100 could include any number of each component. Also, various components in FIG. 1 could be combined, subdivided, or omitted and additional components could be added according to particular needs. In addition, the placement of various components is for illustration only.

FIG. 2 illustrates an example SISO model predictive control scheme 200 for a medication delivery system according to this disclosure. In this control scheme 200, the device controller 116 includes a model relationship 202 defining how a physical characteristic of a patient 106 or, more generally, a physical characteristic of a generic patient varies upon the administration of one or more medications. For example, the model relationship 202 can define how the blood glucose level or other characteristic of the patient 106 can change, both with and without insulin or other medication. The model relationship 202 could be specific to an individual patient 106 or valid for a group of patients 106.

The SISO model predictive control scheme 200 may operate as follows. The device controller 116 receives sensor measurements 204 of a patient's physical characteristic from the patient monitor 102. The device controller 116 uses the model relationship 202 and the sensor measurements 204 to estimate how the patient's physical characteristic may change in the future and whether that change would cause the physical characteristic to move outside of a desired range 206 (which might include only a single value). If the patient's physical characteristic is estimated to move outside of the desired range 206, the device controller 116 can use the model relationship 202 to estimate how much medication to deliver to the patient 106 in order to bring the patient's actual or estimated physical characteristic back into the desired range 206. Effectively, the control algorithm uses measurements of the patient's physical characteristic to compute an optimal control move using the dynamics of the identified model relationship 202 to maintain the patient's physical characteristic within the specified range 206. The algorithm uses the model prediction results and optimizes the solution to minimize the output move. This could be accomplished, for example, using range control as described in U.S. Pat. No. 5,351,184. The algorithm can therefore minimize the amount of medication needed in order to keep one or more characteristics of the patient from falling outside of a desired range. The algorithm also ensures that any constraints are obeyed, such as a maximum amount of medication that can be dispensed at any one time or over a period of time.

As a particular example, the device controller 116 may receive measurements 204 of the patient's blood glucose level, and the model relationship 202 can be used to estimate how the patient 106 or a generic patient responds to insulin. The device controller 116 can determine whether the actual measurements fall outside of a desired range 206 of glucose levels. The device controller 116 can also use the model relationship 204 and the actual measurements to predict whether the patient's blood glucose level may move outside the desired range 206 within a window of time. If the patient's actual or estimated blood glucose level is outside of the desired range 206, the device controller 116 uses the model relationship 202 to determine how much insulin to administer in order to bring the patient's actual or estimated blood glucose level back within the desired range 206. The device controller 116 can then cause the medication reservoir and pump 114 to deliver the desired amount of medication to the patient 106. If the patient's blood glucose level is already in the desired range 206 and is not predicted to leave the desired range 206, the device controller 116 could choose to administer no medication to the patient 106. The device controller 116 can also ensure that any constraints are followed, such as maximum insulin usage per hour or per day.

In this example, one or more disturbances 208 can affect the control of medication delivery. The disturbances 208 here include model mismatch and one or more unmeasured variables. Model mismatch refers to the model relationship 202 not precisely modeling the actual behavior of the patient 106. Model mismatch could be caused by various factors. For instance, the model as designed may fail to accurately predict how the patient's body reacts to medication. Model mismatch could also occur or worsen over time, such as when an accurate model becomes inaccurate due to changes in the patient's physical condition. Unmeasured variables represent one or more variables that affect a controlled characteristic of the patient (such as blood glucose level) but that are not accounted for by the model relationship 202. As a result, changes in an unmeasured variable can affect the patient's reaction to medication but may not be predicted by the device controller 116.

In some embodiments, it is possible to generate a generic model relationship 202 based on, for example, simulations and measured data from multiple patients. For some or many patients, the generic model relationship 202 may be adequate, and the disturbances 208 may be minor and not interfere with the delivery of medication to those patients. In other embodiments, a patient-specific model relationship 202 could be used for an individual patient 106. The patient-specific model relationship 202 may model how that specific patient's body reacts to medication. In still other embodiments, a combination of approaches could be used. For instance, a generic model relationship 202 could be used for a time for a patient 106, and a more patient-specific model relationship 202 could be created later if the disturbances 208 interfere with the delivery of medication to that patient. The patient-specific model relationship 202 could be generated using the data collected during use of the generic model relationship 202.

A patient-specific model could be generated based on measured data for a specific patient 106, such as measured data generated by the patient monitor 102 and collected by the medication delivery unit 104. A patient-specific model could also be generated by using one or more patient parameters 210 to tune a generic model 212. The patient parameters 210 could include any parameters related to the patient 106, such as age, height, weight, body mass, or physical condition. The patient parameters 210 could also include any parameters related to the patient's medical treatment, such as average blood glucose level. The generic model 212 could then be tuned using the patient parameters 210 to generate a model relationship 202 that is more specific to the individual patient 106. Note that any other suitable technique could be used to generate a generic, patient-specific, or other model relationship 202.

In this way, a model relationship 202 suitable for use with a patient 106 can be identified. The model relationship 202 is used with a single input (measurements 204 from the patient monitor 102) to generate a single output (a control signal 214 for the pump 114). The logic used to implement the control algorithm is computationally efficient and therefore suitable for use in a portable device. The logic used to implement the control algorithm can also accommodate many of the complexities of the human body that can affect control of medication delivery using the model relationship 202.

Note that the constraints programmed into or otherwise used by the medication delivery unit 104 could be used to limit the operation of the control logic. For example, the constraints can limit the medication delivered by the control logic of the medication delivery unit 104. The constraints can also be used when the control logic cannot be used, such as when communication with the patient monitor 102 is lost and the sensor measurements 204 are unavailable. In this case, the constraints can be used to control the delivery of medication until communication with the patient monitor 102 is restored.

Although FIG. 2 illustrates one example of a SISO model predictive control scheme 200 for a medication delivery system, various changes may be made to FIG. 2. For example, the model relationship 202 can be generated in any suitable manner, whether internal to or external of the device controller 116 or the medication delivery unit 104. As a particular example, the supply of patient parameters 210 and the tuning of the generic model 212 could occur within the device controller 116 or the medication delivery unit 104. The supply of patient parameters 210 and the tuning of the generic model 212 could also occur outside of the device controller 116 and the medication delivery unit 104, where the resulting model relationship 202 is then downloaded into or otherwise provided to the medication delivery unit 104.

FIG. 3 illustrates an example method 300 for medication delivery using SISO model predictive control according to this disclosure. As shown in FIG. 3, a model is obtained by a medication delivery unit at step 302. This could include, for example, providing a generic or patient-specific model relationship 202 to the device controller 116 of the medication delivery unit 104 for storage in the memory 118. This could also include the device controller 116 or other component generating the model relationship 202 in the medication delivery unit 104.

Sensor measurements are generated for the patient at step 304, and the sensor measurements are received at the medication delivery unit at step 306. This could include, for example, the patient monitor 102 generating blood glucose readings or other sensor measurements and transmitting the measurements wirelessly to the medication delivery unit 104.

The medication delivery unit uses the sensor measurements and at least one model to predict one or more characteristics of the patient at step 308. This could include, for example, the device controller 116 in the medication delivery unit 104 using the model relationship 202 to estimate how the patient's blood glucose level might vary during a specified period of time based on past sensor measurements. The medication delivery unit determines if any predicted characteristic is outside of a desired range at step 310. This could include, for example, the device controller 116 determining if the patient's blood glucose level is predicted to exceed a maximum threshold or fall below a minimum threshold. If not, the method 300 returns to step 304 to continue monitoring the patient.

If the medication delivery unit determines that a patient's characteristic is predicted to move outside of a desired range, the medication delivery unit determines an amount of at least one medication to deliver to the patient at step 312, and the determined amount of medication is delivered at step 314. This could include, for example, the device controller 116 using the model relationship 202 to determine how much medication (and optionally which kind of medication) to supply to the patient 106 in order to bring the patient's monitored characteristic(s) back within range. This could also include the device controller 116 causing the pump 114 to provide the determined amount of medication to the patient 106.

Various optional steps may also occur at some point during the method 300. For example, information could be received from a user (such as the patient) and used to adjust control of the medication delivery at step 316. This could include, for example, the patient 106 adjusting the performance ratio of the control algorithm executed by the device controller 116. Also, a determination can be made whether the current model used by the medication delivery unit is acceptable at step 318. This could include, for example, the device controller 116 tracking how well a predicted characteristic of the patient 106 matches an actual characteristic of the patient 106. If the model is not acceptable, a new model could be obtained at step 320. The new model could be generated internally within the medication delivery unit 104 or received from an external source.

Although FIG. 3 illustrates one example of a method 300 for medication delivery using SISO model predictive control, various changes may be made to FIG. 3. For example, while shown as a series of steps, various steps in FIG. 3 could overlap, occur in parallel, occur in a different order, or occur any number of times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
receiving measurements from a sensor associated with a patient at a portable medication delivery device; and
controlling delivery of medication to the patient at the portable medication delivery device using a single input, single output (SISO) model predictive control technique that includes:
predicting a characteristic of the patient using the measurements and a model associated with the patient;
determining whether the characteristic of the patient is predicted to fall outside of a desired range; and
if the characteristic of the patient is predicted to fall outside of the desired range, determining an amount of medication to deliver to the patient and automatically delivering the determined amount of medication to the patient, wherein determining the amount of medication to deliver comprises predicting an effect the amount of medication will have on the characteristic of the patient based on the model and estimating the amount of medication to return the characteristic of the patient to the desired range using the predicted effect and the model;
after delivery of at least a portion of the amount of medication to the patient, determining how closely an actual effect the amount of medication has on the characteristic of the patient tracks with the predicted effect; and
in response to determining that a difference between the actual effect and the predicted effect exceeds a threshold, identifying a new model to use in predicting the characteristic of the patient,
wherein the amount of medication automatically delivered to the patient always satisfies one or more constraints associated with at least one of a maximum amount or a minimum amount of medication.

2. The method of claim 1, wherein:
a single input of the SISO model predictive control technique comprises the measurements from the sensor; and
a single output of the SISO model predictive control technique comprises a control signal for controlling a pump that delivers the medication to the patient.

3. The method of claim 1, wherein the model comprises a generic model associated with data from multiple patients.

4. The method of claim 3, further comprising:
replacing the generic model with a patient-specific model associated with the individual patient; and
controlling the delivery of medication to the patient using the patient-specific model.

5. The method of claim 1, wherein controlling the delivery of medication to the patient further comprises:
minimizing the amount of medication needed in order to prevent the characteristic of the patient from falling outside of the desired range; and
ensuring that no more than the maximum amount of medication is delivered to the patient within a predetermined time period.

6. The method of claim 1, further comprising:
receiving input from the patient, the input adjustably defining a performance ratio of the SISO model predictive control technique;
wherein the adjustably defined performance ratio defines a speed at which the model predictive control technique responds to changes in the measurements from the sensor.

7. The method of claim 1, wherein:
the measurements from the sensor comprise blood glucose levels of the patient; and
controlling the delivery of medication to the patient comprises controlling delivery of insulin to the patient.

8. An apparatus comprising:
at least one interface configured to receive measurements from a sensor associated with a patient; and
a controller configured to control delivery of medication to the patient using a single input, single output (SISO) model predictive control technique that includes:
predicting a characteristic of the patient using the measurements and a model associated with the patient;
determining whether the characteristic of the patient is predicted to fall outside of a desired range; and
if the characteristic of the patient is predicted to fall outside of the desired range, determining an amount of medication to deliver to the patient and automatically initiating delivery of the determined amount of medication to the patient, wherein the controller is configured to predict an effect the amount of medication will have on the characteristic of the patient based on the model and estimate the amount of medication to return the characteristic of the patient to the desired range using the predicted effect and the model;
after delivery of at least a portion of the amount of medication to the patient, determining how closely an actual effect the amount of medication has on the characteristic of the patient tracks with the predicted effect; and
in response to determining that a difference between the actual effect and the predicted effect exceeds a threshold, identifying a new model to use in predicting the characteristic of the patient,
wherein the controller is configured to determine the amount of medication to deliver to the patient such that the amount of medication automatically delivered to the patient always satisfies one or more constraints associated with at least one of a maximum amount or a minimum amount of medication.

9. The apparatus of claim 8, wherein:
a single input of the SISO model predictive control technique comprises the measurements from the sensor; and
a single output of the SISO model predictive control technique comprises a control signal for controlling a pump that delivers the medication to the patient.

10. The apparatus of claim 8, wherein the model comprises a generic model associated with data from multiple patients.

11. The apparatus of claim 10, wherein the controller is further configured to:
replace the generic model with a patient-specific model associated with the individual patient; and
control the delivery of medication to the patient using the patient-specific model.

12. The apparatus of claim 11, wherein the controller is further configured to generate the patient-specific model.

13. The apparatus of claim 8, wherein the controller is configured to control the delivery of medication to the patient further by:
- minimizing the amount of medication needed in order to prevent the characteristic of the patient from falling outside of the desired range; and
- ensuring that no more than the maximum amount of medication is delivered to the patient within a predetermined time period.

14. The apparatus of claim 8, wherein:
- the controller is further configured to receive input from the patient, the received input adjustably defining a performance ratio of the SISO model predictive control technique; and
- the adjustably defined performance ratio defines a speed at which the model predictive control technique responds to changes in the measurements from the sensor.

15. The apparatus of claim 8, wherein:
- the measurements from the sensor comprise blood glucose levels of the patient; and
- the controller is configured to control delivery of insulin to the patient.

16. A non-transitory computer readable medium embodying a computer program, the computer program comprising computer readable program code for:
- receiving measurements from a sensor associated with a patient at a portable medication delivery device; and
- controlling delivery of medication to the patient at the portable medication delivery device using a single input, single output (SISO) model predictive control technique that includes:
  - predicting a characteristic of the patient using the measurements and a model associated with the patient;
  - determining whether the characteristic of the patient is predicted to fall outside of a desired range; and
  - if the characteristic of the patient is predicted to fall outside of the desired range, determining an amount of medication to deliver to the patient and automatically delivering the determined amount of medication to the patient, wherein the computer readable program code for determining the amount of medication to deliver comprises computer readable program code for predicting an effect the amount of medication will have on the characteristic of the patient based on the model and estimating the amount of medication to return the characteristic of the patient to the desired range using the predicted effect and the model;
  - after delivery of at least a portion of the amount of medication to the patient, determining how closely an actual effect the amount of medication has on the characteristic of the patient tracks with the predicted effect; and
  - in response to determining that a difference between the actual effect and the predicted effect exceeds a threshold, identifying a new model to use in predicting the characteristic of the patient,
- wherein the amount of medication automatically delivered to the patient always satisfies one or more constraints associated with at least one of a maximum amount or a minimum amount of medication.

17. The non-transitory computer readable medium of claim 16, wherein:
- a single input of the SISO model predictive control technique comprises the measurements from the sensor; and
- a single output of the SISO model predictive control technique comprises a control signal for controlling a pump that delivers the medication to the patient.

18. The non-transitory computer readable medium of claim 16, further comprising:
- computer readable program code for receiving input from the patient, the input adjustably defining a performance ratio of the SISO model predictive control technique;
- wherein the adjustably defined performance ratio defines a speed at which the model predictive control technique responds to changes in the measurements from the sensor.

19. The non-transitory computer readable medium of claim 16, wherein:
- the measurements from the sensor comprise blood glucose levels of the patient; and
- the computer readable program code for controlling the delivery of medication to the patient comprises computer readable program code for controlling delivery of insulin to the patient.

20. The non-transitory computer readable medium of claim 16, further comprising:
- computer readable program code for replacing a generic model with a patient-specific model associated with the patient.

* * * * *